United States Patent [19]

Collonge et al.

[11] 4,316,996

[45] Feb. 23, 1982

[54] DISCOLORATION PREVENTION OF PHENOLIC ANTIOXIDANTS

[75] Inventors: Jacques H. Collonge, Les Ulis, France; Hans Widmer, Bottmingen, Switzerland

[73] Assignee: The Goodyear Tire & Rubber Company, Akron, Ohio

[21] Appl. No.: 207,111

[22] Filed: Nov. 17, 1980

[51] Int. Cl.³ .................... C07C 37/11; C07C 29/94; C07C 39/06
[52] U.S. Cl. .................................. 568/784; 568/701; 568/702; 568/785; 568/788; 568/790; 568/793; 568/743; 568/744
[58] Field of Search .............. 568/790, 757, 794, 701, 568/702, 793, 784, 785, 788, 743, 744

[56] References Cited

U.S. PATENT DOCUMENTS 3,946,086 3/1976 Gershanov ......................... 568/794
3,989,665 11/1976 Hollingshead .................. 260/49.95
4,071,565 1/1978 Hollingshead ...................... 568/743
4,152,531 5/1979 Hollingshead ...................... 568/793

Primary Examiner—Werren B. Lone
Attorney, Agent, or Firm—D. O. Nickey

[57] ABSTRACT

Detrimental color change of phenolic antioxidants during production, storage and use in rubbers is inhibited by adding during the synthesis of the phenolic antioxidant a disubstituted hydroxylamine to the catalyst neutralization solution and a substituted oxime together with a disubstituted hydroxylamine to the reaction mixture prior to filtration.

17 Claims, No Drawings

DISCOLORATION PREVENTION OF PHENOLIC ANTIOXIDANTS

TECHNICAL FIELD

This invention pertains to phenolic antioxidants which are of particular use in the rubber industry. More particularly this invention relates to color stabilization of phenolic antioxidant and rubbers stabilized with phenolic antioxidants.

Phenolic antioxidants of various types have found wide acceptance in the area of polymer stabilization. Preferred phenolic antioxidants are those which not only produce good antioxidant activity but which also have a reduced tendency to discolor.

Phenolic antioxidants are commonly added to the rubber latex before coagulation and drying. Variations in the colors of these rubbers due to the discoloration of the antioxidant detracts from the commercial value of such rubbers. Colors ranging from light tan or pink to dark green have been noted and are theorized to result from the oxidation of the phenolic antioxidant. This invention relates to a process for inhibiting the formation of these colors in rubber and more particularly relates to a process of improving the color stability of phenolic antioxidants.

BACKGROUND ART

Hindered phenolic compounds are known in the art as antioxidants for the protection of organic substrates susceptible to deterioration resulting from oxidative aging. These phenolic compounds prevent the chain reaction of oxidative degradation by donating a hydrogen atom to the peroxy radical present. The resulting antioxidant radical is well stabilized and sterically hindered and thus prevented from acting as an initiator of further degradation.

All types of rubber, in particular rubbers formed from dienes, need to be protected from degradation resulting from exposure to oxygen and heating during finishing and storage. Presently alkylation and/or aralkylation products of phenols and cresols are being successfully used for this purpose. With the trend to lighter colored rubbers the discoloration of some of these antioxidants has become detrimental to the value of such rubbers. It is, therefore, desirable that the color and color stability of these phenolic antioxidants be improved and that their tendency to tint and/or discolor the final product be reduced.

During the synthesis of phenolic antioxidants it is known that treatment of the phenolic antioxidant reaction mixture with a phosphite will prevent discoloration of the antioxidant, however, the protection afforded by the phosphite is removed as soon as water is involved in the processing due to hydrolysis of phosphite in water. In the synthesis of phenolic antioxidants the reaction between the phenolic compound and the olefin (for example, isobutylene, diisobutylene, styrene, α-methylstyrene or dicyclopentadiene) is carried out in a one or two-step procedure to produce a multi-component reaction product possessing good antioxidant activity.

The reaction is usually conducted according to conventional alkylation procedures used in the preparation of alkylated phenols. See for example, U.S. Pat. Nos. 4,071,565 and 3,989,665.

U.S. Pat. No. 4,152,531 (which is herein incorporated by reference) discloses an improved process for preparing phenolic antioxidants with superior color properties. The improvement being obtained by carefully controlling process variables such as the temperature of the reaction, moisture level and catalyst level. However, U.S. Pat. No. 4,152,531 does not disclose or suggest that substituted hydroxylamines and/or oximes can be added to the phenolic antioxidant during its synthesis to provide improved color stability.

DISCLOSURE OF INVENTION

In a process of preparing phenolic antioxidants which comprises (1) reacting one mole of at least one phenolic reactant having the following structural formula:

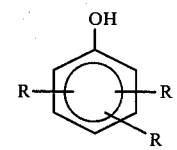

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms, with (2) at least one tertiary olefin having from 4 to 9 carbon atoms at a temperature of from 50° C. to 150° C. in the presence of a catalyst; then (3) the catalyst is neutralized with an aqueous solution and (4) the reaction mixture is heated under vacuum to remove volatiles and filtered hot; the improvement is characterized in that (A) 0.01 to 5 percent by weight of at least one disubstituted hydroxylamine of general formula (I) and/or (II):

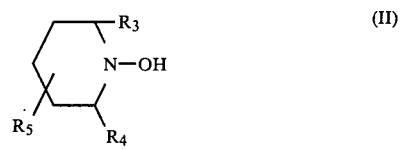

wherein $R_1$ and $R_2$ are the same or different radicals selected from the group consisting of alkyl radicals of 1 to 18 carbon atoms; and $R_3$, $R_4$ and $R_5$ are the same or different radicals selected from the group consisting of hydrogen and alkyl radicals of 1 to 8 carbon atoms; is added to the solution used to neutralize the catalyst and (B) prior to filtration 0.01 to 5 percent by weight of a substituted oxime of the structural formula (III):

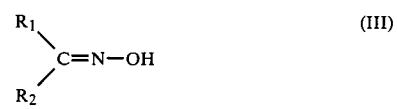

wherein $R_1$ and $R_2$ are defined as above is added to the reaction mixture together with an additional 0.01 to 5.0 percent by weight of a substituted hydroxylamine of formula (I) and/or (II); to yield a phenolic antioxidant with improved color and color stability.

MORE DETAILED DISCLOSURE

The present invention includes situations where an olefin is reacted with a phenolic reactant within the practice of the present invention and the reaction product is further alkylated with another tertiary olefin to produce a trisubstituted phenolic reaction product.

Where an olefin containing 8 or 9 carbon atoms is used, the reaction is essentially a one-step reaction where all of the olefin is added within a temperature range of from about 50° C. to about 150° C.

When it is desired to produce a trisubstituted phenolic reaction product, and an olefin containing 8 or 9 carbon atoms is used, preferably the said olefin is used in a two-step reaction where the said olefin is reacted in the first step and an olefin containing 4 to 7 carbon atoms is reacted in the second step.

When an olefin containing 8 or 9 carbon atoms is used in a two-step reaction it is added in the first step, and an olefin containing 4 to 7 carbon atoms is added in the second step, the reaction temperature of the first step is from about 50° C. to about 150° C. and the temperature of the second step is from about 30° C. to about 90° C.

In a two step process of preparing phenolic antioxidant compositions comprising (1) reacting in the first step the composition comprising (a) one mole of at least one phenolic reactant having the following structural formula:

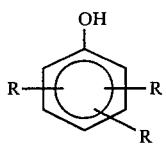

wherein R is selected from the group consisting of hydrogen alkyl radicals having from 1 to 20 carbon atoms, cycloalkyl radicals having from 6 to 20 carbon atoms, and aralkyl radicals having from 6 to 20 carbon atoms, with (b) at least one tertiary olefin having from 8 to 9 carbon atoms at a temperature of from 50° C. to 150° C. in the presence of a catalyst and then the reaction product is (2) reacted in the second step with at least one tertiary olefin having from 4 to 7 carbon atoms at a temperature of 30° to 90° C.; and then (A) the catalyst is neutralized with an aqueous solution and (B) the reaction mixture is heated under vacuum to remove volatiles and filtered hot; the improvement is characterized in that (1) at least one disubstituted hydroxylamine of general structural formula (I) and/or (II):

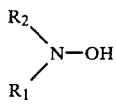

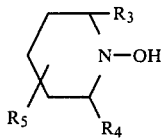

wherein $R_1$ and $R_2$ are the same or different radicals selected from the group consisting of alkyl radicals of 1 to 18 carbon atoms; and $R_3$, $R_4$ and $R_5$ are the same or different radicals selected from the group consisting of hydrogen and alkyl radicals of 1 to 8 carbon atoms; is added to the aqueous solution used to neutralize the catalyst and (2) addition of a substituted oxime of the structural formula (III)

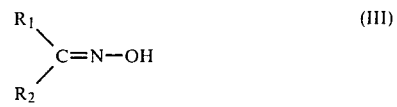

wherein $R_1$ and $R_2$ are defined as above; together with an additional amount of a substituted hydroxylamine of formula (I) and/or (II) to the reaction mixture prior to filtration, to yield a phenolic antioxidant with improved colored and color stability.

The preferred disubstituted hydroxylamine is diethylhydroxylamine and the preferred substituted oxime is methylethyl ketoxime. In other words, the process of this invention is accomplished by adding a substituted hydroxylamine to the water used in the neutralization of the catalyst and by adding prior to filtration a substituted oxime and an additional quantity of substituted hydroxylamine to the reaction mixture to provide improved color and color stability to the antioxidant.

It is during the preparation of phenolic antioxidants that the process of this invention is used. The alkylation catalyst employed to catalyze the process is normally neutralized with a suitable basic material such as sodium carbonate solution. It is at this point in the synthesis of the phenolic antioxidant that 0.01 to 5 percent by weight substituted hydroxylamine is added to the neutralization water which contains a suitable basic material such as sodium carbonate. This is done to protect the phenolic antioxidant during the neutralization. During filtration an additional amount of the hydroxylamine is added together with the oxime to protect the antioxidant during filtration and storage.

Prior to filtration 0.01 to 5% by weight substituted oxime and an additional 0.01 to 5.0% by weight substituted hydroxylamine is added to the reaction mixture. The second addition of the hydroxylamine is required due to the fact that it has been removed during neutralization and distillation. This later addition protects the phenolic antioxidant during filtration and storage and inhibits the formation of color bodies during the coagulation and drying of rubber latices containing such stabilizers. It is the addition of these compounds during the preparation of phenolic antioxidants that leads to a decrease or elimination of coloration of the phenolic antioxidant. In addition, the process of this invention provides the phenolic antioxidant with a longer shelf life due to the increased stability of the phenolic antioxidant. It is this decrease in the oxidation of the phenolic antioxidant during storage and use that leads to a decrease or elimination of color formation after combination of the antioxidant with the organic material to be protected. The following example is included for illustration of the practice of the present invention and is intended to exemplify but not to limit the practice of the present invention.

EXAMPLE 1

The preparation of phenolic antioxidants has been modified by the addition of two reducing agents. This process has proved to significantly reduce the discoloration of organic materials stabilized with phenolic antioxidants. The production of an antioxidant as described in U.S. Pat. No. 4,152,531, column 6, lines 43 through 68 was followed until stage two which is the neutralization step.

The procedure consists of reacting phenol with diisobutylene and isobutylene in the following amounts.

|  | Amount Part by Weight |
| --- | --- |
| Phenol | 94 |
| Diisobutylene | 224 |
| Isobutylene | 56 |

The toluene sulfonic acid catalyst was added to the phenol and water added to obtain 1.6% by weight. Diisobutylene was added over a 3½ hour period at 100° C. and allowed to stir for 15 minutes after addition was complete. The reaction mixture was cooled to 60° C. and isobutylene added at 60° C.±2° C. The catalyst was destroyed with aqueous Na₂CO₃ containing 0.5% by weight diethylhydroxylamine.

Prior to filtration, 2 percent by weight methylethyl ketoxime and another 0.2 percent by weight diethylhydroxylamine was added to the reaction mixture prior to filtration.

TEST DATA

To test the effectiveness of the process of the present invention a phenolic antioxidant was produced using the process as described in Example I and aged in a hot air oven at 85° C. for 4 days. A a control the same antioxidant was produced but without addition of 0.5% by weight diethylhylhydroxylamine to the catalyst neutralization water and without addition of 2% by weight methylethyl ketoxime and 0.2% by weight diethylhydroxylamine to the reaction mixture, prior to filtration.

TABLE I

| Day | Antioxidant from Example I Color Gardner Scale | Antioxidant Control Color Gardner Scale |
| --- | --- | --- |
| 0 | <1 | 3 (pink) |
| 1 | 1–2 | 7–8 |
| 2 | 2 | 7–8 |
| 3 | 3–4 | 7–8 |
| 4 | 5–6 | 7–8 |

The test results demonstrate that the process of the present invention provides an antioxidant that initially has better color properties and tends to discolor less than an antioxidant that is prepared without using the process of the present invention.

Experimentation has also determined that when antioxidants prepared utilizing the process of the present invention are incorporated into rubber, the amount and rate of discoloration is reduced.

For example, the color of air dried SBR 1500 after coagulation that has 1 part per hundred by weight of the antioxidant control (as in the test data) had a green color while the antioxidant prepared according to Example I produced a SBR with a pale cream color at the same concentration.

INDUSTRIAL APPLICABILITY

The use of the process of this invention will prevent or greatly lessen the discoloration of phenolic antioxidants during preparation and storage. In addition, the use of this invention will also prevent or lessen the discoloration of the organic material protected by the phenolic antioxidant in that oxidation and subsequent discoloration of the phenolic antioxidant has been eliminated or at least reduced. It is, therefore, evident that a process which alleviates the problems of antioxidant discoloration and product discoloration has advantages over what is presently known in the art.

While certain representative embodiments and details have been shown for the purpose of illustrating the invention, it will be apparent to those skilled in this art that various changes and modifications may be made therein without departing from the spirit or scope of the invention.

We claim:

1. In a process of preparing phenolic antioxidants which comprises (1) reacting one mole of at least one phenolic reactant having the following structural formula:

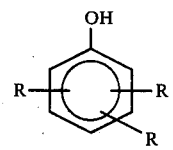

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms, with (2) at least one tertiary olefin having from 4 to 9 carbon atoms at a temperature of from 50° C. to 150° C. in the presence of a catalyst; then (3) the catalyst is neutralized with an aqueous solution and (4) the reaction mixture is heated under vacuum to remove volatiles and filtered hot; the improvement is characterized in that (A) 0.01 to 5 percent by weight of at least one hydroxylamine selected from general formulae (I) and (II).

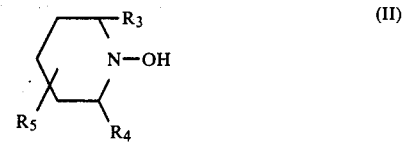

wherein $R_1$ and $R_2$ are the same or different radicals selected from the group consisting of alkyl radicals of 1 to 18 carbon atoms; and $R_3$, $R_4$ and $R_5$ are the same or different radicals selected from the group consisting of hydrogen and alkyl radicals of 1 to 8 carbon atoms; is added to the solution used to neutralize the catalyst and (B) prior to filtration 0.01 to 5 percent by weight of a substituted oxime of the structural formula (III):

wherein $R_1$ and $R_2$ are defined as above is added to the reaction mixture together with an additional 0.01 to 5.0 percent by weight of at least one hydroxylamine selected from formulae (I) and (II); to yield a phenolic antioxidant with improved color and color stability.

2. In a process according to claim 1 wherein the disubstituted hydroxylamine is diethylhydroxylamine and the substituted oxime is methylethyl ketoxime.

3. The process according to claim 1 wherein the process is conducted in one-step and the tertiary olefin contains 8 or 9 carbon atoms and the temperature ranges from about 50° C. to 150° C.

4. The process according to claim 1 wherein the process is conducted in two steps, the first step comprising (1) reacting in the first step the composition comprising (a) one mole of at least one phenolic reactant having the following structural formula:

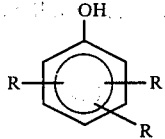

wherein R is selected from the group consisting of hydrogen, alkyl radicals having from 1 to 20 carbon atoms, cycloalkyl radicals having from 6 to 20 carbon atoms, and aralkyl radicals having from 6 to 20 carbon atoms, with (b) at least one tertiary olefin having from 8 to 9 carbon atoms at a temperature of from 50° to 150° C. in the presence of a catalyst and (2) the second step comprises reacting the reaction product of step one with at least one tertiary olefin having from 4 to 7 carbon atoms at a temperature of 30° to 90° C.

5. In a process according to claim 3 wherein the disubstituted hydroxylamine is diethylhydroxylamine and the substituted oxime is methylethyl ketoxime.

6. In a process according to claim 4 wherein the disubstituted hydroxylamine is diethylhydroxylamine and the substituted oxime is methylethyl ketoxime.

7. A process according to claim 1 wherein the hydroxylamine of formula (I) is (A) added to the solution to neutralize the catalyst and (B) is added with a compound of formula (III) to the reaction mixture prior to filtration.

8. A process according to claim 1 wherein the hydroxylamine of formula (II) is (A) added to the solution used to neutralize the catalyst and (B) is added with a compound of formula (III) to the reaction mixture prior to filtration.

9. A process according to claim 1 wherein the hydroxylamine of formula (I) is (A) added to the solution used to neutralize the catalyst and (B) the hydroxylamine of formula (II) is added with a compound of formula (III) to the reaction mixture prior to filtration.

10. A process according to claim 1 wherein the hydroxylamine according to formula (II) is (A) added to the solution to neutralize the catalyst and (B) the hydroxylamine of formula (I) is added with a compound of formula (III) to the reaction mixture prior to filtration.

11. A process according to claim 1 wherein the hydroxylamine of formula (I) is (A) added to the solution used to neutralize the catalyst.

12. A process according to claim 1 wherein the hydroxylamine of formula (II) is (A) added to the solution used to neutralize the catalyst.

13. A process according to claim 1 wherein the hydroxylamine of formula (I) is (B) added with a compound of formula (III) to the reaction mixture prior to filtration.

14. A process according to claim 1 wherein the hydroxylamine of formula (II) is (B) added with a compound of formula (III) to the reaction mixture prior to filtration.

15. A process according to claim 1 wherein 0.02 to 4 percent by weight of at least one hydroxylamine of general formulae (I) and (II) is (A) added to the solution used to neutralize the catalyst and (B) added to the reaction mixture prior to filtration.

16. A process according to claim 1 wherein 0.03 to 3 percent by weight of at least one hydroxylamine of general formulae (I) and (II) is (A) added to the solution used to neutralize the catalyst and (B) added to the reaction mixture prior to filtration.

17. A process according to claim 1 wherein (A) 0.5 percent by weight diethylhydroxylamine is added to the solution used to neutralize the catalyst and (B) 2 percent by weight methylethyl ketoxime and 0.2 percent by weight of diethyl hydroxylamine is added to the reaction mixture prior to filtration.

* * * * *